United States Patent [19]
Aylsworth et al.

[11] Patent Number: 5,911,219
[45] Date of Patent: Jun. 15, 1999

[54] THERAPEUTIC GAS FLOW METER AND MONITOR

[76] Inventors: Alonzo C. Aylsworth, 19359 Ossenfort Rd., Glencoe, Mo. 63038; Charles Graham, 2470 Doris Dr., Arnold, Mo. 63010; Gregory R. Miller, #4 Morganfield Ct., Chesterfield, Mo. 63005

[21] Appl. No.: 08/839,799

[22] Filed: Apr. 18, 1997

[51] Int. Cl.$^6$ .................................................. A61M 16/00
[52] U.S. Cl. .............................. 128/205.23; 128/203.24; 73/861.56
[58] Field of Search .................. 128/205.23, 204.13, 128/204.14, 203.24, 205.24; 600/529; 73/861.55, 861.56, 861.57

[56] References Cited

U.S. PATENT DOCUMENTS

| | | |
|---|---|---|
| 2,073,372 | 3/1937 | Heidbrink ............................ 128/205.23 |
| 2,463,473 | 3/1949 | Boothby ............................... 128/205.23 |
| 3,550,355 | 12/1970 | Remus et al. . |
| 3,726,270 | 4/1973 | Griffis et al. . |
| 3,930,814 | 1/1976 | Gessner . |
| 4,096,746 | 6/1978 | Wilson et al. . |
| 4,300,548 | 11/1981 | Jones ................................... 128/205.23 |
| 4,421,529 | 12/1983 | Revak et al. . |
| 4,457,303 | 7/1984 | Durkan . |
| 4,462,398 | 7/1984 | Durkan et al. . |
| 4,516,424 | 5/1985 | Rowland . |
| 4,545,790 | 10/1985 | Miller et al. . |
| 4,561,287 | 12/1985 | Rowland . |
| 4,627,860 | 12/1986 | Rowland . |
| 4,630,486 | 12/1986 | Miles et al. ........................... 73/861.56 |
| 4,648,888 | 3/1987 | Rowland . |
| 4,677,975 | 7/1987 | Edgar et al. . |
| 4,681,099 | 7/1987 | Sato et al. . |
| 4,686,975 | 8/1987 | Naimon et al. . |
| 4,822,384 | 4/1989 | Kato et al. . |
| 4,844,059 | 7/1989 | Koch . |
| 5,053,058 | 10/1991 | Mitariten . |

(List continued on next page.)

FOREIGN PATENT DOCUMENTS

| | | |
|---|---|---|
| 57-71804 | 5/1982 | Japan . |
| 59-55390 | 3/1984 | Japan . |
| 60-11206 | 1/1985 | Japan . |
| 64-7001 | 2/1989 | Japan . |
| 6277433 | 4/1994 | Japan . |
| 8704354 | 7/1987 | WIPO . |
| 9010470 | 9/1990 | WIPO . |
| 9106334 | 10/1990 | WIPO . |

OTHER PUBLICATIONS

"The Measurement of Oxygen in Gas Mixtures," The Institute of Physics, 1986, pp. 401–412.

*Primary Examiner*—John G. Weiss
*Assistant Examiner*—V. Srivastava
*Attorney, Agent, or Firm*—Paul M. Denk

[57] ABSTRACT

A flow meter has a body, an inlet operatively connected to a source of gas, and an outlet. A valve for opening and closing the outlet is provided which includes a valve seat, a valve shaft movable axially relative to the valve seat and a valve member on the valve shaft. The valve member movable by axial translation of the valve shaft between a first position in which the valve member engages the valve seat to close the outlet and a second position in which the valve member is spaced from the valve seat to allow gas to pass through said outlet. The flow meter further includes a sensor which senses the position of said valve member relative to said valve seat and generates a signal indicative of said position. In one embodiment, the sensor comprises an infrared light emitter and an infrared photo-detector positioned on opposite sides of the valve member, which is preferably conical. Depending on the axial position of the valve member, the amount of light which reaches the photodetector changes. In another embodiment, the valve shaft is operable connected to a potentiometer which is responsive to the rotational position of the valve shaft, and hence the axial position of the valve member. In a third embodiment, a magnet is placed about the valve shaft, and a magnetic field detector is placed within the magnets magnetic field. The sensor is responsive to the position of the magnet and hence the position of the valve member.

5 Claims, 6 Drawing Sheets

U.S. PATENT DOCUMENTS

| | | |
|---|---|---|
| 5,060,514 | 10/1991 | Aylsworth . |
| 5,071,453 | 12/1991 | Hradek et al. . |
| 5,099,698 | 3/1992 | Kath et al. .......................... 73/861.56 |
| 5,134,995 | 8/1992 | Gruenke et al. . |
| 5,137,017 | 8/1992 | Salter . |
| 5,266,101 | 11/1993 | Barbe et al. . |
| 5,281,253 | 1/1994 | Thompson . |
| 5,363,842 | 11/1994 | Mishelevich et al. . |
| 5,373,851 | 12/1994 | Reinhold, Jr. et al. ................. 600/529 |
| 5,379,651 | 1/1995 | Doolittle .............................. 73/861.56 |
| 5,439,507 | 8/1995 | Barbe et al. . |
| 5,470,379 | 11/1995 | Garrett . |
| 5,474,595 | 12/1995 | McCombs . |
| 5,495,848 | 3/1996 | Aylsworth et al. . |
| 5,496,388 | 3/1996 | Tellier . |
| 5,529,607 | 6/1996 | Tan . |
| 5,531,218 | 7/1996 | Krebs . |
| 5,531,807 | 7/1996 | McCombs . |
| 5,544,533 | 8/1996 | Sugi et al. .......................... 73/861.56 |
| 5,593,478 | 1/1997 | Hill et al. . |

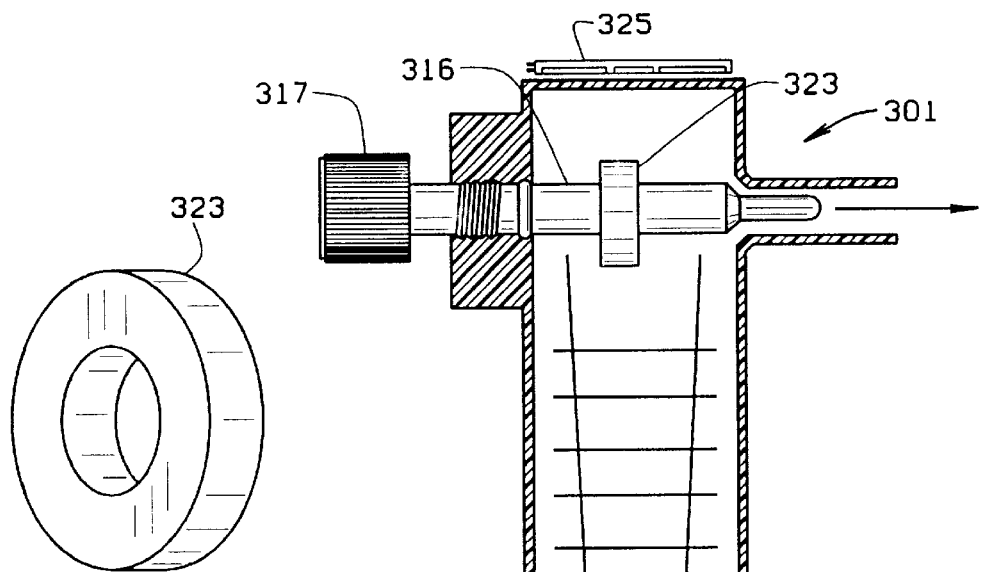
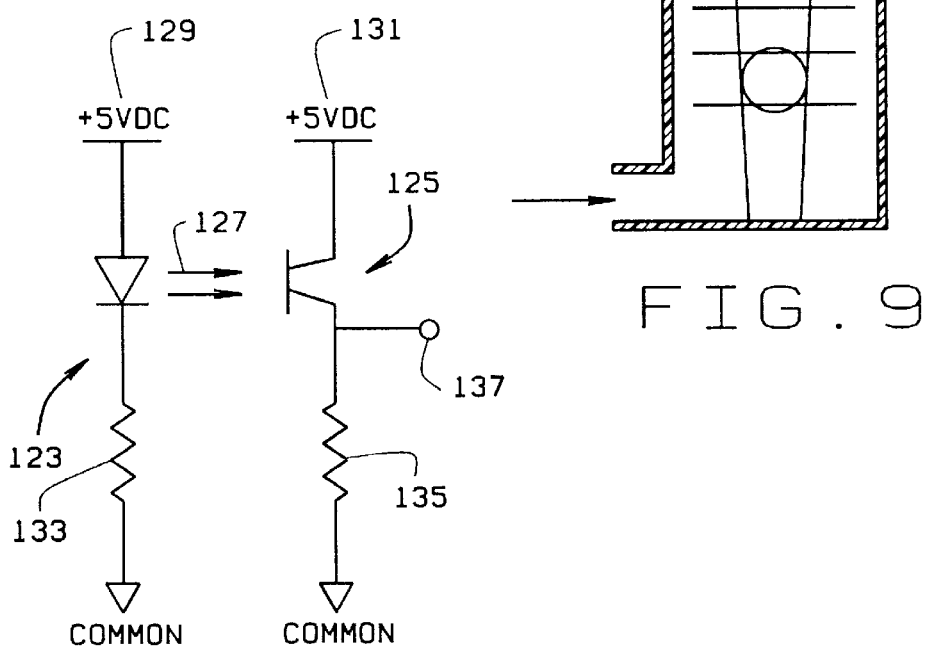

THERAPEUTIC GAS FLOW METER AND MONITOR

CROSS-REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

This invention relates to a therapeutic gas flow meter and, in particular to a flow meter which monitors the flow setting and flow adjustments made by a patient or user of therapeutic gas.

Generally, a patient with a pulmonary breathing disorder or oxygen deficiency is required to breath oxygen provided from a source of oxygen to increase the level, or amount of oxygen they breath in from the atmosphere. The patient is given a prescription that indicates the concentration of oxygen, the flow or volume requirement of oxygen, and the use of the oxygen, for example, the hours per day of oxygen delivery. In some cases, the prescription will include the precise hours of the day the patient is to receive the oxygen therapy. For example the patient's prescription may call for two liters of oxygen per minute for two hours during the day and eight hours at night. Or, in some cases, the prescription may call for four liters of oxygen per minute for twenty-four hours a day. Usually the prescription is based upon oxygen requirements established in a controlled setting, such as at a hospital during hospitalization. The prescription is continued at home after the patient is discharged from the hospital. Delivery of oxygen therapy at home should correspond to the prescription developed in the hospital. Failure to comply with the prescription could be harmful to the patient or less beneficial than planned.

Oxygen concentrators have been developed and commercialized to provide the delivery of near pure oxygen to the individual patient to satisfy medical needs. These concentrators can be small and portable. However, once the patient leaves the controlled setting of the hospital, it is difficult to monitor the patient's use of the oxygen to ensure that he is complying with the prescription. An important part of a patient's therapeutic gas prescription is the flow amount or rate. Thus, it is important to know at which level the patient has set his therapeutic gas meter and equally important to know when and to what amount an adjustment is made.

The preferred therapeutic gas source generally is an oxygen concentrator. Other therapeutic gas sources can of course be used. The gas source normally uses an adjustable flow meter having a ball indicator so that the user can read the flow rate. Two common flow meters found in oxygen concentrators are those manufactured by Key Instruments of Trevose, Pa., under Part #FO43, and by Dwyer Instruments of Michigan City, Ind., under Part #59-700360-00. A typical flow meter 1 is shown in FIGS. 1 and 2. The flow meter 1 includes a meter body 3 having an inlet port 5, and outlet port 7, and a Thorpe Tube 9 between the inlet and outlet through which the gas flows. An indicator ball 11 floats in the Thorpe Tube 9 and is elevated or floated in the Thorpe Tube by the flow of gas through the tube 9. The level to which the ball 11 is raised is indicative of the flow rate of gas through the meter. An indicating scale 13 is provided to allow a user to read the flow rate. A user adjustable metering valve 15 is operated by a knob 17 to alter the flow through the meter. Typically, the valve 15 is a needle valve, and includes a needle portion 19 which extends forwardly of a shaft 20 and into the throat 21 of the outlet 7. The valve shaft is threaded, as at 23. The threads 23 are received in an internally threaded boss 25. An O-ring 27 is provided to prevent gas from escaping out through the boss. Thus, as can be appreciated, by rotating the knob 17, the needle 19 moves axially to be inserted into, or pulled away from, the throat 21, to open or close the outlet 7.

Operation of this type of flow meter is simplistic and well known in the art. Therapeutic gas enters inlet port 5 travels through Thorpe Tube 9 causing the indicator ball 11 to rise to a level which is proportional to the amount of therapeutic gas flow which exits at the outlet port 7. When the user desires to control the flow of therapeutic gas the patient adjusts the user adjustable metering valve knob 17 alters the degree to which the throat 21 is open, to decrease or increase the therapeutic gas flow to the desired level as indicated by the alignment of the indicator ball 11 on the indicating scale 13. Typically the user rotates the user adjustable metering valve knob 17, in a clockwise direction to restrict the flow of therapeutic gas to a lesser amount and likewise the user may adjust the metering valve knob 17 counter-clockwise for a greater amount of therapeutic gas flow.

Flow information is normally only available by reading the ball indicator on the flow meter. When it is desired to obtain flow information via electronic means an electronic flow sensing means must be added to the meter. Flow sensing means and the use of flow sensors to monitor the flow of a gas through a meter are known. However, we know of no sensors which monitor the setting of the meter. When using an oxygen concentrator, it may be necessary to monitor the valve setting independently of the flow rate. In these cases it is necessary to not only monitor flow settings but also to log into memory flow setting data to communicate this data to a care giver.

BRIEF SUMMARY OF THE INVENTION

In accordance with the invention, generally stated, a flow meter is provided with a sensor to measure the setting of the flow meter, as compared to the flow rate of gas flowing through the flow meter. The flow meter has a body, in inlet operatively connected to a source of gas, an outlet, and a valve for opening and closing the outlet. The valve includes a valve seat, a valve shaft movable axially relative to the outlet and a valve member on the valve shaft. The valve member is movable between a first position in which the valve member engages the valve seat to close the outlet and a second position in which the valve member is spaced from the valve seat to allow gas to pass through the outlet. The sensor generates a signal indicative of the position of the valve shaft and hence the valve seat.

In accordance with one aspect of the invention, the sensor comprises an emitter which produces an infra-red light beam and a photodetector which detects infra-red light. The emitter and detector are positioned in the meter on opposite sides of the valve member such that the detector can detect light transmitted by the emitter. The valve member has a tapered surface such that, as the valve shaft, and hence the valve member translate axially relative to the valve seat, the amount of light emitted by the emitter which reaches the detector varies.

In another aspect of the invention, the sensor comprises a potentiometer have a rotatable shaft which is coupled to the valve shaft. The connection between the valve shaft and the potentiometer shaft allows the valve shaft to translate axially without moving the potentiometer. This will allow the potentiometer to be fixed or mounted, for example, to a circuit board. The potentiometer generates a signal indicative of the rotational position of the valve shaft, and hence of the setting of the valve member.

In another variation, the sensor comprises an annular magnet fixed to the valve shaft at a desired axial location along the valve shaft and a magnetorestrictive sensor which detects the magnitude of the magnetic field produced by the magnet. The magnetorestrictive sensor is positioned externally of the flow meter and within the magnetic field. As the valve shaft and valve member translate axially, the position of the magnet, and hence the magnetic field move relative to the magnetorestrictive sensor. Therefore, the magnitude of the field detected by the magnetorestrictive sensor will vary in accordance with the position of the magnet, and hence the valve shaft.

In accordance with another aspect of the invention, the flow meter includes a microprocessor having a data storage device which stores the signal generated by the sensor as well as the prescription information. The microprocessor is provided with a comparator and an alarm. The comparator compares the real time data to the prescription information, and if the real time data does not correspond to the prescription, the alarm is activated. The flow meter can also be provided with communication means, such as a modem, for example. The communication means can be activated at the same time the alarm is activated to alert a care giver of the out-of-prescription condition of the flow meter. The communication means can also be used to transmit the information stored in the data storage device to a desired location, so that the care giver can review the patient's compliance with the prescription.

BRIEF DESCRIPTION OF THE SEVERAL VIEWS OF THE DRAWINGS

FIG. 6 is an electrical schematic of the setting sensor of FIG. 4;

FIG. 9 is a schematic cross-sectional view of a third alternative setting sensor of the present invention which uses a magnetorestrictive element;

FIG. 10 is a perspective view of the magnetorestrictive element of FIG. 9; and

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode of carrying out the invention.

Figures 1, 2:
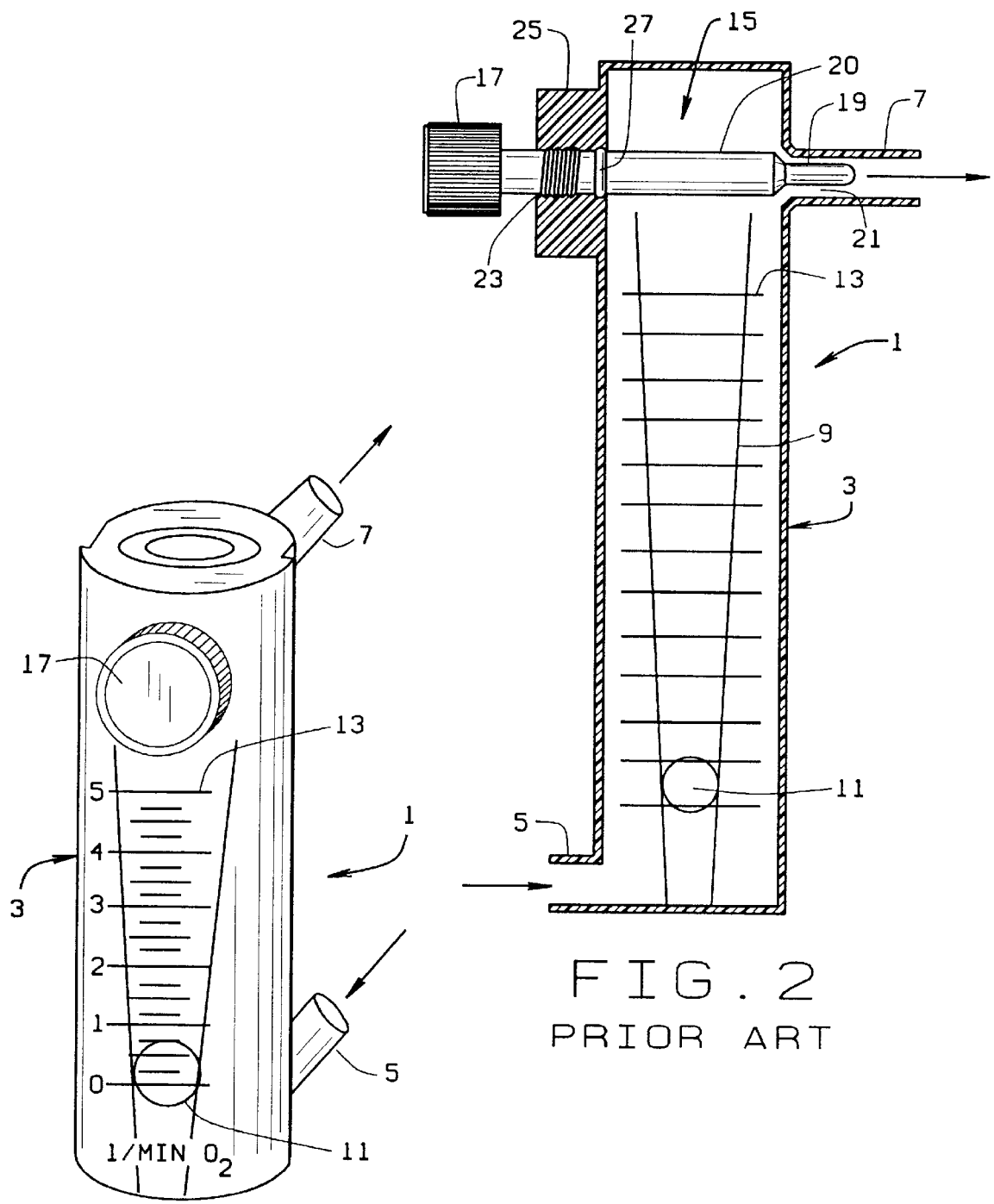
FIG. 1 is a perspective view of a prior art flow meter.
FIG. 2 is a cross-sectional view of the prior art flow meter.
Figure 3:
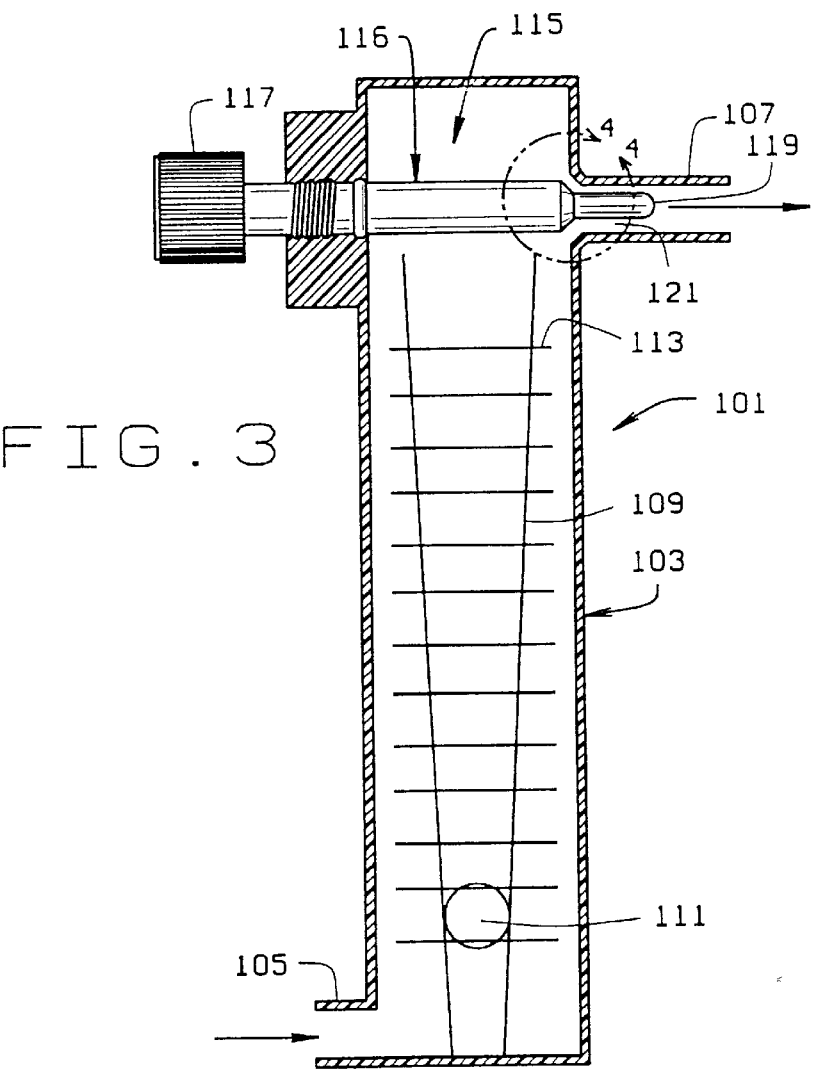
FIG. 3 is a cross-sectional view of a flow meter of the present invention.
Figure 4:
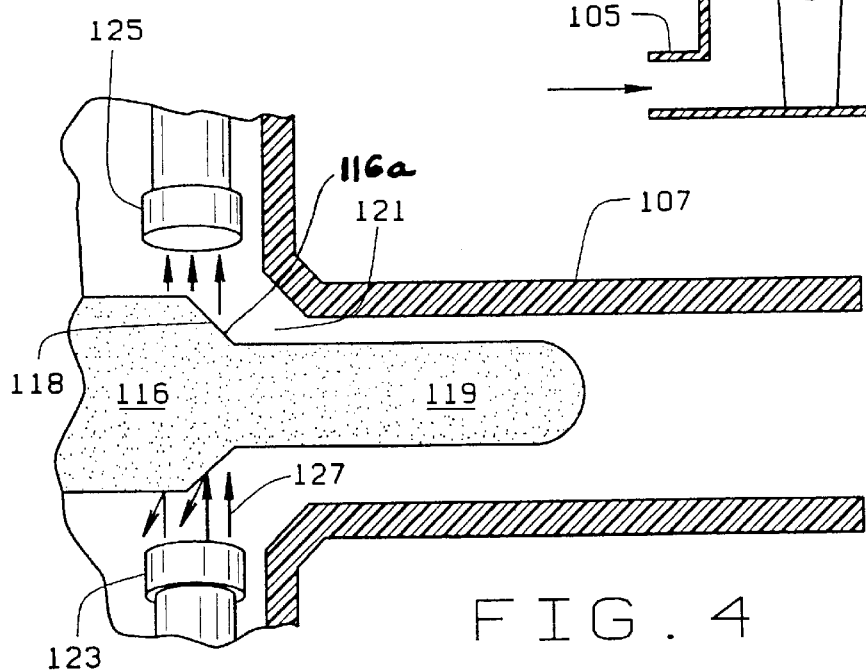
FIG. 4 is an enlarged cross-sectional view of one embodiment of a setting sensor of the present invention.
Figure 5:
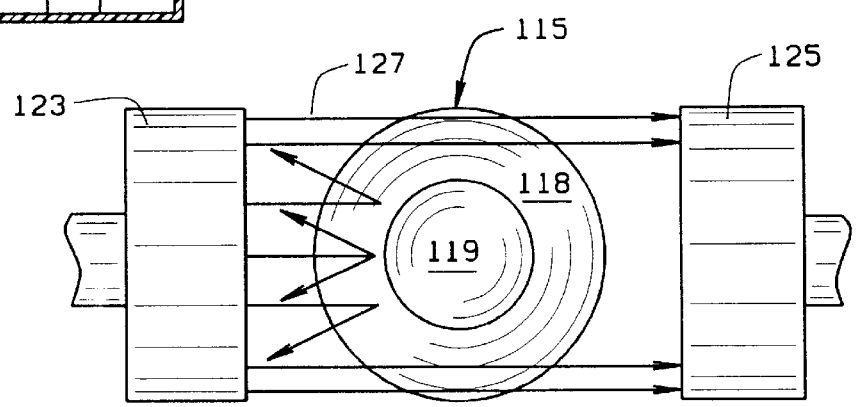
FIG. 5 is an enlarged front plan view of the setting sensor of FIG. 4.

A first illustrative embodiment of a flow meter 101 of the present invention is shown in FIGS. 3–5. The flow meter 101 is substantially similar to the flow meter 1 and includes a body 103 having an inlet 105, an outlet 107, and a Thorpe Tube 109 between the inlet and outlet. A float ball 111 and indicator marks 113 are provided for a visual determination of the flow rate. As with the flow meter 1, the flow meter 101 includes a needle valve 115 operable by a knob 117 to increase or decrease the size of the throat 121 into the outlet 107. The valve 115 includes a valve shaft 116 which steps down at 118 to a needle portion 119, and as before, the needle portion is received in the throat 121 of the outlet 107. As can be appreciated, the shape of the throat 121 corresponds to the shape of the sloped portion 118 of the shaft 116. Thus, the throat 121 defines a seat for the valve 115 and the sloped portion 118 of the shaft 116 defines a valve element which, when its valve member 116a is engaged with the valve seat (throat 121), closes the outlet 107.

To monitor or sense the setting of the valve, the meter 101 is provided with an infra-red emitter 123 and an infra-red photodetector 125. The infra-red emitter 123 is one such as is commonly available from Digi Key of Thief River Falls, Minn., under part #LT1028. The infra-red photodetector 125, is also commonly available from Digi Key as part #LT1030. The emitter 123 generates an infra-red light beam 127 which is detected by the photodetector 125. The photodetector 125, in turn, generates an electrical signal indicative of the amount of light which impinged on the detector. The emitter 123 and detector 125 are positioned on opposite sides of the valve shaft 116, such that as the knob 117 is turned, the transition area 118 of the valve 115 will move across the path of light. As can be appreciated, as the valve is closed, the amount of light 127 which will reach the detector 125 will decrease, the light being deflected off the transition portion 118 of the valve 115, as seen in FIG. 5. Conversely, when the valve is opened, the amount of light which reaches the detector 125 will increase.

In operation the position of mechanical metering valve shaft 116 is proportional to the flow setting selected by the user. Both the infra-red emitter 123 and the infra-red photodetector 125 are embedded into the flow-meter assembly 101, or mounted within the flow meter assembly. Thus, when the valve shaft 116 is fully retracted (i.e., the throat 121 is fully open), a large amount of infra-red light will reach the photodetector 125. This large amount of infra-red light beam transmission would indicate flow settings correspond to abnormal therapeutic gas settings. The user would adjust the user adjustable metering valve knob 117 clockwise for the desired level of therapeutic gas flow as prescribed by physician. The output of the detector 125 can be operatively connected to an alarm, so that when the too high or too low flow levels are detected, the alarm can be sounded to alert the user to change the flow setting.

As the mechanical metering valve shaft 116 moves from left to right (with reference to FIGS. 3 and 4) to close the valve, the infra-red light beam 127 becomes blocked thus reducing the amount of infra-red light beam 127 detected at infra-red photodetector 125. Thus, the flow setting made by the user affects the position of the mechanical metering valve shaft 116 and causes corresponding infra-red light beam 127 to be partially blocked. The amount of light which reaches the detector 125 is proportional to the flow setting.

FIG. 6 is a simple schematic of the emitter 123 and detector 125 of the sensor. As shown, the emitter 123 and detector 125 include associated power sources 129 and 131 and resistors 133 and 135. The detector 125 also includes a voltage output 137 through which the signal generated by the detector is transmitted. The power supplies 129 and 131 are +5 VDC sources, and may be a single source for both the emitter and the detector. The resistor 133 is preferably a 332Ω resistor and serves to limit the amount of current flowing through the infra-red emitter 123. The resistor 135 is preferably a 249Ω resister, and in conjunction with infra-red photodetector 125 provides a voltage divider network that creates an output voltage at 137 which is proportional to the amount of light received at infra-red photodetector 125.

To ensure a constant level of brightness from emitter 123, a constant current source, such as Part #TL43 1 available from Motorola and associated circuitry, could be substituted for the resistor 133. It is possible to provide an additional infra-red photodetector to allow for a calibration check of the system, thereby assuring a constant brightness or light level from infra-red emitter 123. Then any change in the system dynamics from the second infra-red photodetector would be evident as a measurable change in the normal difference of the voltage output of the devices. This could result in activation of an alarm which would notify the patient and/or the caregiver that the flow is in an out-of-tolerance situation.

Figure 7:
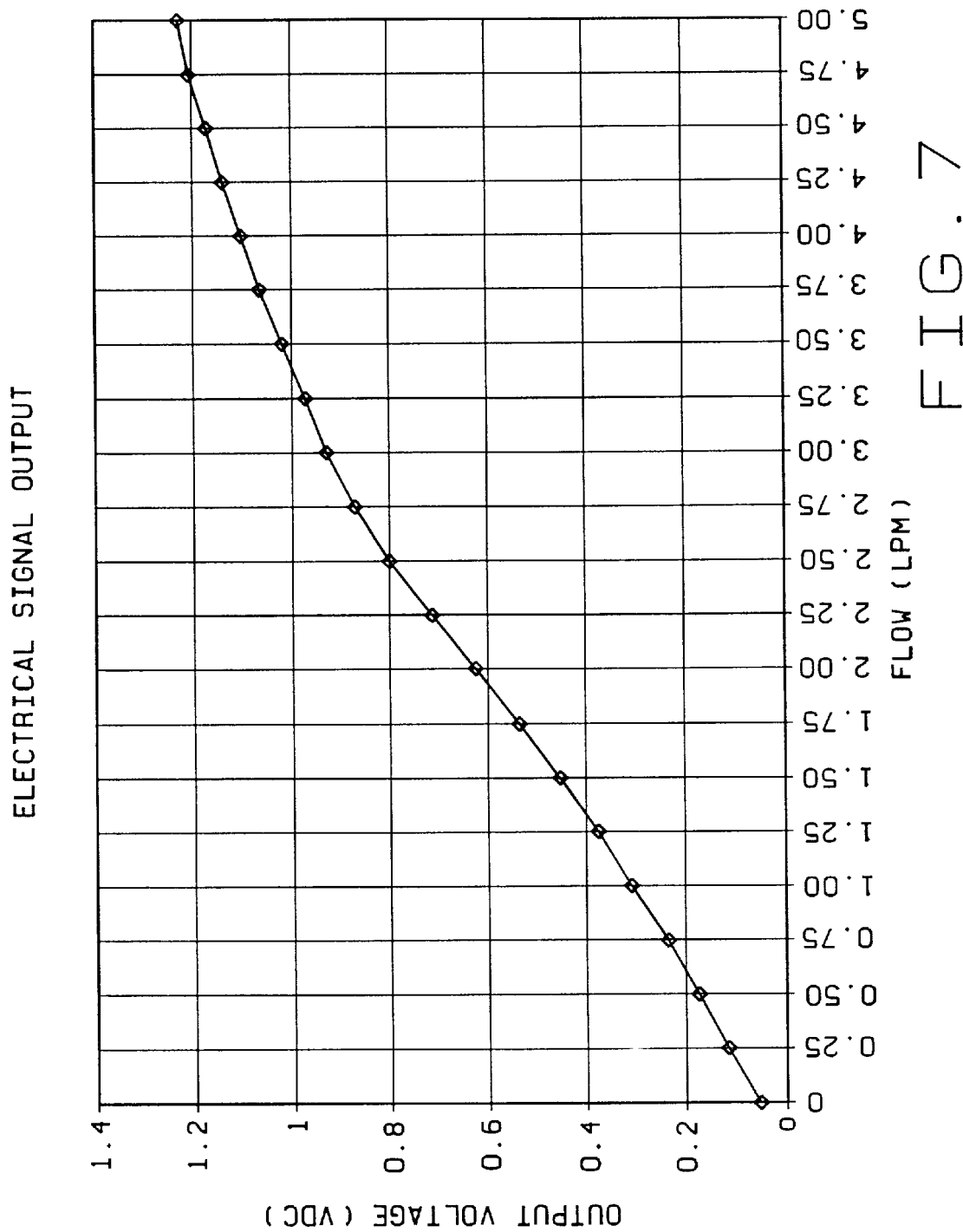
FIG. 7 is a graph of the electrical signal output by the setting sensor of FIG. 4.

FIG. 7 is a graph of the unamplified voltage output produced by the system schematically shown in FIG. 6. This output voltage could be processed using commonly available electronic means to provide a more linear output which could be utilized for further processing to achieve other functions, such as flow setting alarm levels. One method of processing the voltage output by the detector 125 would be to incorporate a microprocessor, such as Motorola of Phoenix, Ariz., Part #MC74HC05P6.

Figure 8:
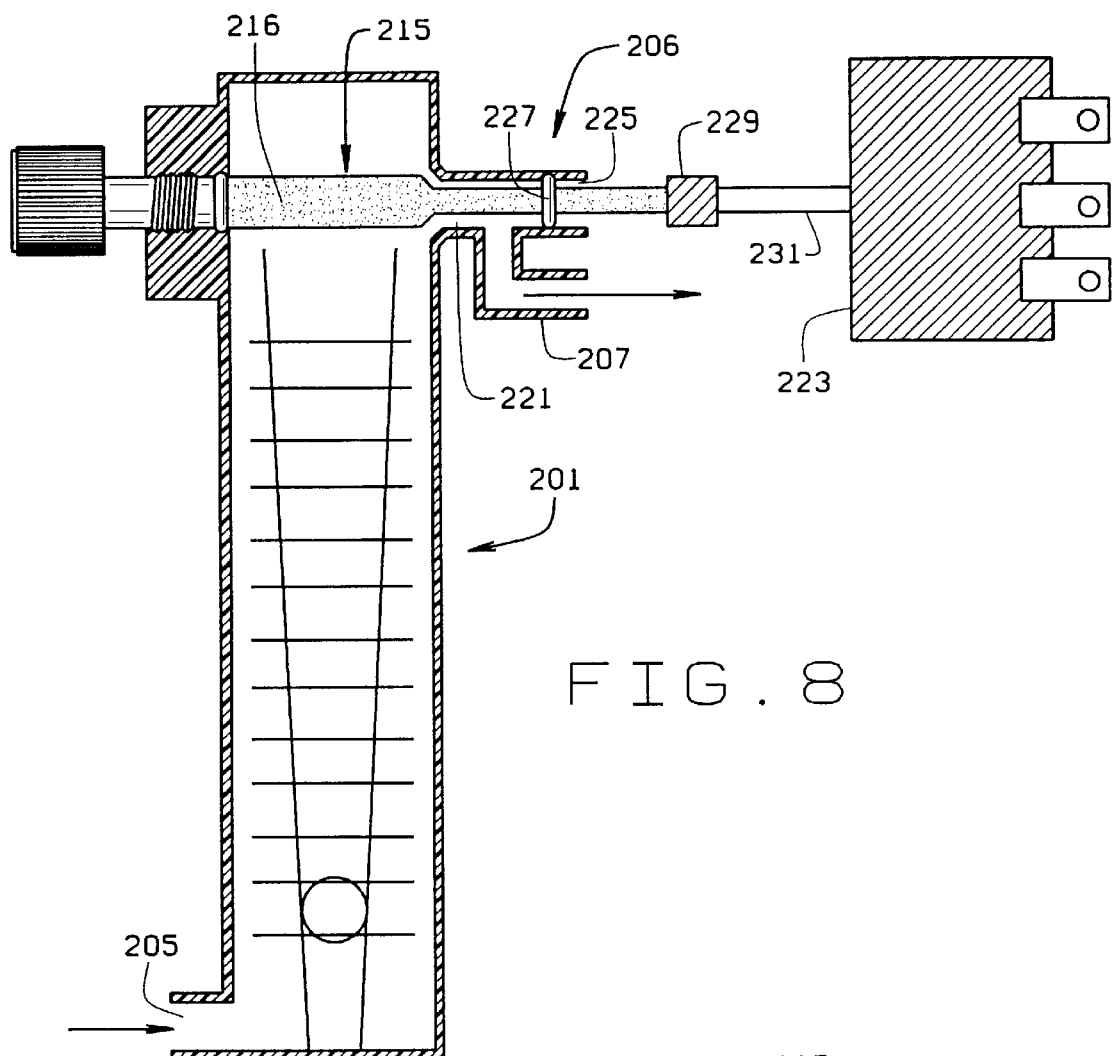
FIG. 8 is a schematic cross-sectional view of an alternative setting sensor of the invention which uses a potentiometer.

A second therapeutic gas electronic flow meter/monitor 201 is shown in FIG. 8. The flow meter/monitor 201 is based upon the basic design of the meters 1 and 101. However, the outlet 207 is modified, as will be discussed. The flow meter/monitor 201 uses a potentiometer 223 as the sensor to monitor the setting of the valve 215. Operation of the flow meter/monitor 201 is similar to the operation of a typical flow meter 1, however the outlet port 206 has been modified to a generalize "S" shape to allow the valve shaft 216 to be extended. The valve shaft 216 exits through a shaft exit 225 and an O-ring 227 is provided around the shaft 216 to prevent the gas from escaping through the shaft exit 225. The gas exit 207 is formed as an "L" depending from the shaft exit 225 and is positioned after the throat 221 of the valve 215. Thus, the therapeutic gas will exit through port 207, after it passes through the throat 221.

A shaft coupler 229 connects the valve shaft 216 to a shaft 231 of the potentiometer 223. The coupler 229 is connected to the end of shaft 216 such that rotation of the shaft will rotate the coupler, so that the rotational position of the shaft 216 can be mechanically transmitted to the potentiometer 223. However, the connection between the coupler 229 and the shaft 216 allows for axial translation of the shaft 216 relative to the coupler 229, so that as the shaft translates axially, the coupler will not move axially. Such a connection can be made, for example, using a key and slot arrangement, wherein a slot is formed in the coupler and a key radiates from the shaft to be received in the slot. This type of connection is desirable if the potentiometer 223 is to be rigidly mounted to an electronic circuit board or mechanical mounting bracket. The coupler 229 also allows for perpendicular movement of the extended metering valve shaft 216 so as not to interfere with normal operation of flow setting by the user.

The potentiometer 223 provides an output in responsive to, and indicative of, the position of valve shaft 216. The output can be a analog voltage output. In some instances it is desirable to obtain a digital output of flow setting. In such cases the use of an optical binary encoder maybe substituted for setting potentiometer 223. The optical encoder is available from Digi Key as Part #CT3003-ND. This type of encoder would indicate sixteen flow setting positions. Other encoders are available which will provide greater resolution for example, 128 flow setting positions are available.

Still another method of measuring the flow setting is to use the Giant Magnetoresistive Ratio (GMR) method of linear detection. Referring to FIGS. 9 and 10, the flow meter 301 is based on the meter 1 previously described. The mechanical metering valve shaft 316, preferably manufactured out of stainless steel, has a donut shaped or annular magnet 323 fixed to the shaft 316 at a desired location along the shaft. The magnet 323 extends around the shaft, as seen in FIG. 9. The donut magnet 323 is one such as is available from McMaster Carr of Chicago, Ill., Part #5902K55. A giant magnetoresistive ratio (GMR) sensor 325, such as is commonly available from Nonvolatile Electronics Inc. of Eden Prairie, Minn., as Part #NV55B 10051, is installed externally of the flow meter assembly 301, but within the magnetic field generated from the donut magnet 323. The sensor 325 is preferably installed on the top of the flow meter assembly 301, as shown in FIG. 9.

In operation, the linear position of the magnet 323 relative to the sensor 325 is proportional to the flow setting of the meter 301. That is, as the flow setting is changed by rotation of the shaft 316 by rotation of the knob 317, the shaft 316 will move axially, as described above. Because the magnet 323 is fixed relative to the shaft 316, the position of the magnet 323 relative to the sensor 325 will change as the shaft 316 is rotated. This linear motion moves the magnetic field of the donut magnet 323, relative to the sensor 325. Thus, the local strength of the magnetic field at the sensor 325 will change as the magnet 323 is moved. The magnetic field measured by the giant magnetoresistive ratio (GMR) sensor 325 produces an output voltage which is linear and proportional to the flow setting. The giant magnetoresistive ratio (GMR) method produces an unamplified output voltage from about 0 to 250 mv proportional to 0 to 6 LPM with an input voltage of 5 VDC when used with the magnet described herein.

Proper calibration is achieved by the horizontal relationship between the donut magnet 323 and the giant magnetoresistive ratio (GMR) sensor 325. The amount of voltage output depends upon the magnetic strength of the donut magnet 323 and the vertical distance between the magnet 323 and the giant magnetoresistive ratio (GMR) sensor 325.

Those skilled in the art will recognize that other methods of flow setting sensors may be incorporated in lieu of the potentiometer, optical decoder, and magnetorestrictive sensor described above. For example it may be desirable to incorporate a wheel assembly which includes a magnet and a Hall effect sensor to count rotational information and to use memory means to derive the flow setting information. As another example, servo mechanisms could be utilized to obtain flow setting information in response to mechanical flow metering valve shaft rotation. It is common in the art, especially when the therapeutic gas source being used is a liquid oxygen reservoir, to incorporate a flow setting means that uses an adjustable orifice or valve assembly which usually selects the flow of therapeutic gas in ¼ LPM increments. Such flow setting means utilize a series of orifices and assume a relatively fixed operating pressure to obtain the liter flow desired. Thus, it is possible and within the scope of this invention to incorporate rotational flow setting means such as the potentiometer method or optical method onto such an adjustable orifice flow setting means and obtain the desired results of this invention.

Figure 11:
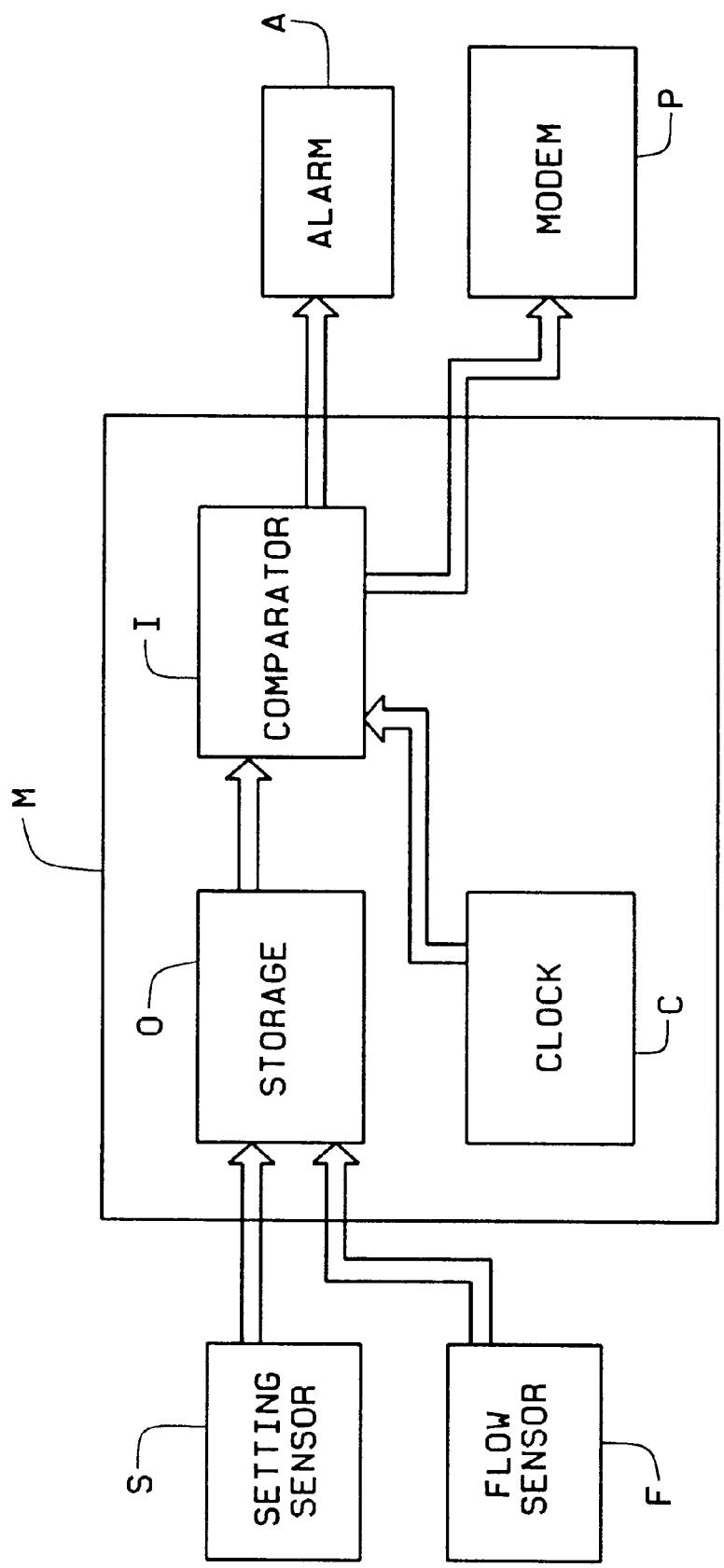
FIG. 11 is a block diagram of the sensors of the present invention and the connection of the sensor to a microprocessor.

Turning to FIG. 11, the flow meter can be provided with an alarm A, such as an audible or visible alarm which is responsive to the signal generated by the sensor S. The sensor S may be any of the above noted sensors. This may be accomplished through commonly available componentry such as with the use of a microprocessor M available from "Motorola" Part #MC74HC05P6, and which is provided with a storage device 0 and a clock C. Additional memory storage S and Clock C circuitry may be provided externally by microprocessor M for more demanding applications of the present invention. The microprocessor M is operable to store the prescription and the readings from the setting sensors S and includes means for converting the sensor signal into information indicative of the setting of the flow meter. The alarm A could be utilized in different ways. For example, if the patients prescription requires a flow setting during a specified time period and the flow setting is adjusted outside of the predetermined time period then all audio and/or visual alarms can be made to alert a patient, or user, or caregiver, of the out of compliance situation. This can be done, for example, by sending the prescription information and the actual data, and a time reading from the clock C to a comparator I. The comparator I will then compare the real time data from the sensor to the prescription information and date/time information. If the real time data does not correspond to what the flow setting should be, based upon the prescription, the comparator will generate a signal to activate the alarm. Also communication means, such as a modem P, can be incorporated to alert a remote station, such as the home care providers. Additional communication of the alarm means may be accomplished through the use of a radio frequency transmission and reception techniques (including pagers), fiber optics techniques, etc.

The use of the microprocessor M and its associated memory storage 0 and date/time circuitry C allows for calibration of the flow meter by software and communication means of the flow setting means and method of flow setting means. This circuitry allows for preprogramming of the alarm levels and the logic to be followed within the alarm means. This circuitry also controls and coordinates the communication means as previously mentioned. Furthermore this circuitry allows the incorporation of historical data consisting of information about calibration, alarm levels, date/time of alarms, and action taken. Date/time of all flow settings and information concerning communications that have taken place may also be logged. The use of the modem or other communication means allows direct communication of historical data from the point of care to a remote location to make the data available for review by a physician or appropriate caregiver at any desired time.

The flow meter could also be equipped with a flow sensor F which would measure the actual flow of therapeutic gas being delivered. This will allow the electronic circuitry incorporating microprocessor and associated memory storage and date/time circuitry to provide additional capability. Specifically, automatic calibration and periodic calibration can be accomplished by comparing the measured value from the flow sensor to the actual flow being measured. Calibration and recalibration as described herein could also be controlled via the communication means. Additionally if a leak in the therapeutic gas patient delivery system occurs causing the actual flow delivered to be different from that of the flow setting then the alarm means including communication means could be activated.

In view of the above, it will be seen that the several objects and advantages of the present invention have been achieved and other advantageous results have been obtained. As various changes could be made in the above constructions without departing from the scope of the invention, it is intended that all matter contained in the above description or shown in the accompanying drawings shall be interpreted as illustrative and not in a limiting sense. Those skilled in the art will recognize that modifications within the scope of this invention may be made for example, just as there are various methods to measure rotational movement which is proportional to the flow setting there are also other methods to measure linear motion which is proportional to the flow setting. A linear velocity displacement transformer could readily measure the position of the valve shaft. Additionally, capacitive proximity sensors could easily measure linear motion proportional to the flow setting.

We claim:

1. A flow meter having a body, an inlet operatively connected to a source of gas, an outlet, and a valve for opening and closing the outlet, the valve including a valve seat, valve shaft movable axially relative to said outlet and a valve member provided on said valve shaft, said valve member movable between a first position in which said valve member engages said valve seat to close said outlet and a second position in which said valve member is spaced from said valve seat to allow gas to pass through said outlet; said flow meter further including a sensor which senses the position of said valve member relative to said valve seat and generates a signal indicative of said position; said sensor comprising a potentiometer having a rotatable shaft, said valve shaft being coupled to said potentiometer shaft such that said valve shaft will translate axially without moving said potentiometer, said potentiometer generating a signal indicative of the rotational position of said valve shaft, and hence of the setting of the valve member.

2. A flow meter having a body, an inlet operatively connected to a source of gas, an outlet, and a valve for opening and closing the outlet, the valve including a valve seat, valve shaft movable axially relative to said outlet and a valve member provided on said valve shaft, said valve member movable between a first position in which said valve member engages said valve seat to close said outlet and a second position in which said valve member is spaced from said valve seat to allow gas to pass through said outlet;

said flow meter further including a sensor which senses the position of said valve member relative to said valve seat and generates a signal indicative of said position;

said sensor comprising an annular magnet fixed to said valve shaft at a desired axial location along said valve shaft and a magnetorestrictive sensor;

said magnet producing a magnetic field, said magnetorestrictive sensor being positioned externally of said flow meter and within said magnetic field, said magnetorestrictive sensor generating an output indicative of the strength of said magnetic field for a specified location in the setting of the said shaft, wherein, when said valve shaft and valve member translate axially, the position of the magnet, and hence the magnetic field, move relative to magnetorestrictive sensor, the signal generated by the magnetorestrictive sensor being indicative of the setting of the position of the valve shaft, and hence the valve member.

3. A flow meter having a body, an inlet operatively connected to a source of gas, an outlet, and a valve for opening and closing the outlet, the valve including a valve seat, valve shaft movable axially relative to said outlet and a valve member provided on said valve shaft, said valve member movable between a first position in which said valve member engages said valve seat to close said outlet, and a second position in which said valve member is spaced from said valve seat to allow gas to pass through said outlet, said flow meter further including a sensor which senses the position of said valve member relative to said valve seat and generates a signal indicative of said position;

said sensor comprising an emitter which produces an infrared light beam and photo detector which detects infrared light, said emitter and detector being positioned in said meter on opposite sides of said valve member, such that said detector can detect light transmitted perpendicularly across said valve member by said emitter, said valve member having a tapered surface such that as said valve shaft, and hence said valve member translate axially relative to said valve seat, the quantity of light emitted by said emitter which reaches said detector varies, said detector generating an output signal indicative of the amount of light which impinges on said detector, and provides an indication of the position of said valve member;

a microprocessor including a data storage device, said microprocessor being operatively connected to said sensor to receive said signal generated by the sensor, said microprocessor including means for converting said signal from said sensor into information indicative of the setting of the flow meter valve shaft through passage of the infrared light beam perpendicularly there across, and wherein said microprocessor stores the information in said storage device.

4. The flow meter of claim 3 wherein said microprocessor includes a comparator and an alarm, said microprocessor storing prescription information in said data storage device, said comparator comparing said setting of the flow meter against said prescription information;

said comparator generating a signal if said information does not correspond to said prescription information, said alarm being responsive to said comparator signal to activate said alarm when said setting information does not correspond to said prescription information.

5. The flow meter of claim 4 herein said microprocessor includes communication means, said communication means being operable to transmit the information store in the data storage device to a remote location.

* * * * *